United States Patent [19]
Walker et al.

[11] Patent Number: 5,284,971
[45] Date of Patent: Feb. 8, 1994

[54] 4-(3-CYCLOHEXYL-4-HYDROXY OR -METHOXY PHENYLSULFONYL) 3,5 DIBROMO PHENYL ACETIC THYROMIMETIC CHOLESTEROL-LOWERING AGENTS

[75] Inventors: Keith A. Walker, Los Altos Hills; Sharada S. Labadie, Sunnyvale; Denis J. Kertesz, Mountain View; Craig W. Laughton, Palo Alto, all of Calif.

[73] Assignee: Syntex (U.S.A.) Inc., Palo Alto, Calif.

[21] Appl. No.: 914,837

[22] Filed: Jul. 16, 1992

[51] Int. Cl.$^5$ .............................. A61K 31/50
[52] U.S. Cl. .................. 562/429; 544/239; 544/240; 546/302; 546/301; 560/11; 560/62; 560/9; 560/17
[58] Field of Search .............. 562/429; 514/568, 570, 514/618, 513, 532

[56] References Cited

U.S. PATENT DOCUMENTS

| | | | |
|---|---|---|---|
| 3,198,702 | 8/1965 | Hellbaum | 514/568 |
| 3,357,887 | 12/1967 | Kagan et al. | 514/568 |
| 3,649,679 | 3/1972 | Marshall | 562/429 |
| 4,125,729 | 11/1978 | Trust et al. | 562/429 |
| 4,156,011 | 5/1979 | Lafon | 562/429 |
| 4,168,385 | 9/1979 | Trust et al. | 560/56 |
| 4,567,279 | 1/1980 | Chan | 514/532 |
| 5,145,611 | 8/1992 | Wolff et al. | 562/429 |
| 5,179,097 | 1/1993 | Angres et al. | 514/570 |

FOREIGN PATENT DOCUMENTS

| | | | |
|---|---|---|---|
| 0060776 | 9/1982 | European Pat. Off. | 514/570 |
| 0188351 | 1/1986 | European Pat. Off. | |
| 2433943 | 4/1980 | France | 514/570 |
| 7209182 | 1/1973 | Netherlands | 514/570 |
| 828766 | 2/1960 | United Kingdom | 514/532 |

OTHER PUBLICATIONS

*Hormonal Proteins and Peptides*, (1978), vol. 6, pp. 59-61, 129-138, 70-71, 149-156, Edited by C. Li. Thyroid Hormones.
*J. Med. Chem.*, (1988), vol. 31, pp. 37-54, P. D. Leeson et al. Thyroid Hormone Analogues. Synthesis of 3'-- Substituted 3,5-Diiodo-L-thyronines and Quantitative Structure-Activity Studies of in Vitro and in Vivo Thyromimetic Activities in Rat Liver and Heart.

(List continued on next page.)

*Primary Examiner*—Donald G. Daus
*Attorney, Agent, or Firm*—William Schmonsees; David A. Lowin; Alan M. Krubiner

[57] ABSTRACT

Compounds of general formula (I)

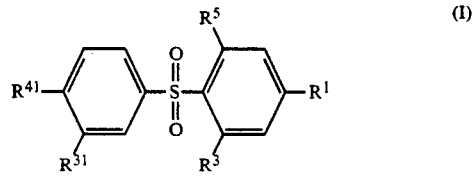

wherein
$R^1$ is $(CH_2)_n((CHNR^7R^8)_mC(O)R^9$; n=1-3; and m=0 or 1;
$R^3$ and $R^5$ are independently Cl, Br, I, or $CH_3$;
$R^7$ and $R^8$ are independently H or $(C_1-C_4)$alkyl;
$R^9$ is OH, $(C_1-C_4)$alkoxy, or $NR^7R^8$;
$R^{31}$ is H, Cl, Br, I, $(C_1-C_4)$alkyl, $(C_4-C_6)$cycloalkyl, $(C_1-C_4)$haloalkyl, $(C_4-C_6)$halocycloalkyl, or $-CH(R^{10})Ar$ where Ar is selected from 5-hydroxypyrid-2-yl, 6-hydroxypyrid-3-yl, 6-hydroxypyridazin-3-yl, 6-methoxypyridazin-3-yl, 6-hydroxypyridazin-3-yl N-oxide, and 6-methoxypyridazin-3-yl N-oxide and $R^{10}$ is H or $(C_1-C_4)$alkyl;
$R^{41}$ is OH or a bioprecursor thereof; and the pharmaceutically acceptable salts thereof; are structural analogs of the thyroid hormones $T_3$ and $T_4$ and exhibit selective thyromimetic activity. Pharmaceutical compositions of the novel compounds and their use for the treatment of mammalian cholesteremia are provided.

2 Claims, No Drawings

OTHER PUBLICATIONS

*J. Med. Chem.,* (1989), vol. 32, pp. 320-334, P. D. Leeson et al. Selective Thyromimetics. Cardiac-Sparing Thyroid Hormone Analogues Containing 3'-Arylmethyl Substituents.

*J. of Bio. Chem.,* (1975), vol. 250, No. 16, pp. 6417-6423, D. Koerner et al. Binding of Selected Iodothyronine Analogues to Receptor Sites of Isolated Rat Hepatic Nuclei.

*Nature,* (1986), vol. 324, pp. 425-429, A. H. Underwood et al. A Thyromimetic that Decreases Plasma Cholesterol Levels without Increasing Cardiac Activity.

*J. of Bio. Chem.,* (1961), vol. 236, No. 11, pp. 2981-2986, K. Tomita et al. Synthesis and Biological Activity of O-Methyl Derivatives of Thyroid Hormones.

*Mayo Clinic Proceedings,* (1987), vol. 39, pp. 609-625, S. B. Barker et al. Some Aspects of Metabolism of Thyroxine and of Analogues Devoid of the Phenolic Group.

4-(3-CYCLOHEXYL-4-HYDROXY OR -METHOXY PHENYLSULFONYL) 3,5 DIBROMO PHENYL ACETIC THYROMIMETIC CHOLESTEROL-LOWERING AGENTS

BACKGROUND OF THE INVENTION a) Field of the Invention

This invention relates to compounds and pharmaceutical compositions useful for treating mammalian cholesteremia.

b) Description of Related Art

The natural thyroid hormones, 3, 3',5-triiodo-L-thyronine ($T_3$) and L-thyroxine ($T_4$), are recognized cholesteremics which, due to their potent effects on cardiac function, are not indicated for the therapeutic reduction of plasma cholesterol levels in euthyroid subjects.

Since Harington and Barger, Biochem. J. 21, 169–181 (1927), first reported the structure and synthesis of thyroxine, numerous studies have been conducted to identify and synthesize structural analogs which mimic the activity of the natural hormones. The comprehensive review by E. C. Jorgensen in Hormonal Proteins and Peptides, Li, C. H., Ed., Academic Press, New York, Vol. VI, Chapters 2 and 3, 57–204 (1978) summarizes the intensive efforts to vary the thyroxine substituent pattern to produce thyromimetics, primarily for thyroid replacement therapy.

The structure of thyroxine provides considerable opportunities for varying the substituent pattern:

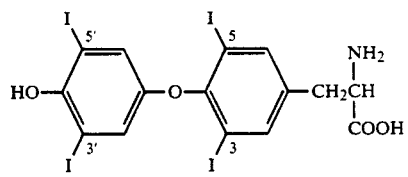

Using rat anti-goiter assays as a touchstone for activity, Jorgensen (vide supra) surmised that certain basic structural characteristics affected activity, as follows:

a) 3,5-disubstitution by size-limited lipophilic groups enhances activity in the order: I>Br>Me=Cl;

b) 3'-substitution by alkyl groups or halogen atoms generally enhances activity in the order: iPr->I>Et>Br>Me>Cl>F>H;

c) halogen substituents are not essential for activity; and d) 5'-substituents decrease activity.

Koerner et al., also relying on rat anti-goiter assays, suggested that the alanine side chain was not necessary to activity and that the O-ether bridge could be replaced by a thioether or methylene bridge. J. Biol. Chem., 250:16, 6417–6423 (1975).

Focusing on the utility of $T_3$ and its analogs as cholesterol-lowering agents, Underwood et al. have reported the preparation of thyromimetics, one of which was as active as $T_3$ on the liver, but had only about 0.1% of the activity of $T_3$ on the heart. Nature 324, 425–429 (1986). These authors concluded that a diphenyl ether core with 4'-OH and 3,5-halogen substitution was essential for high receptor affinity. Such compounds are presumably the subject matter of European Patent Application 0 18 351, published Jul. 23, 1986, in which a number of thyroxine analogs having diphenyl ether cores and 3'-arylalkyl substituents are disclosed.

Leeson, et al. noted that replacement of the 3'-iodo substituent in $T_3$ had been limited to halogen, small alkyl, phenyl, nitro, and hydroxyl until their own investigations of twenty-nine novel 3'-derivatives. J. Med. Chem. 31, 37–54 (1988). Again, the compounds all have diphenyl ether cores.

Leeson, et al. have further reported that introduction of specific 3'-arylmethyl groups gives liver-selective, cardiac-sparing thyromimetics. Modifications to the 3,5-substituents, ether oxygen, and L-alanyl side chain were also disclosed. These authors observed that the ether oxygen may be replaced by sulfur or methylene, which maintain the orthogonal arrangement of the diphenyl aromatic rings. J. Med. Chem. 32, 320–336 (1989).

The disclosures of the aforementioned patents and publications are incorporated by reference herein.

Despite the long-felt need and the above-noted extensive research efforts, little progress has been made in the development of thyromimetics which lower serum cholesterol without adverse cardiac effects.

SUMMARY OF THE INVENTION

The current invention provides a new class of thyromimetics, in which the distinguishing characteristic is the presence of a sulfonyl bridge in the diphenyl core.

The compounds of this invention are of general formula (I),

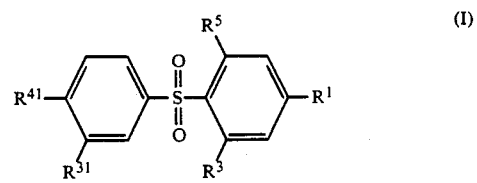

wherein
$R^1$ is $(CH_2)_n(CHNR^7R^8)_mC(O)R^9$; n=1–3; and m=0 or 1;

$R^3$ and $R^5$ are independently Cl, Br, I, or $CH_3$;

$R^7$ and $R^8$ are independently H or ($C_1$–$C_4$)alkyl;

$R^9$ is OH, ($C_1$–$C_4$)alkoxy, or $NR^7R^8$;

$R^{31}$ is H, Cl, Br, I, ($C_1$–$C_4$)alkyl, ($C_4$–$C_6$)cycloalkyl, ($C_1$–$C_4$)haloalkyl, ($C_4$–$C_6$)halocycloalkyl, or —CH($R^{10}$)Ar where Ar is selected from 5-hydroxypyrid-2-yl, 6-hydroxypyrid-3-yl, 6-hydroxypyridazin-3-yl, 6-methoxypyridazin-3-yl, 6-hydroxypyridazin-3-yl N-oxide, and 6-methoxypyridazin-3-yl N-oxide and $R^{10}$ is H or ($C_1$–$C_4$)alkyl;

$R^{41}$ is OH or a bioprecursor thereof; and the pharmaceutically acceptable salts thereof.

The compounds of this invention are structural analogs of $T_3$ and $T_4$ and exhibit selective thyromimetic activity. When tested in vivo, they mimic the cholesterol-lowering effects of the thyroid hormones, with little or no effect on the heart.

This invention further comprises pharmaceutical compositions of the novel compounds and their use in the treatment of disease states characterized by cholesteremia.

A further aspect of this invention is a process for preparing compounds of general formula (I) and salts thereof.

DETAILED DESCRIPTION OF THE INVENTION

Definitions

"Alkyl" refers to a fully saturated, straight or branched chain monovalent hydrocarbon radical, having from one to four carbon atoms, i.e. methyl, ethyl, i-propyl, n-propyl, t-butyl, n-butyl, s-butyl, and isobutyl.

"Alkoxy" refers to a radical of the formula —O-alkyl.

"Haloalkyl" refers to an alkyl radical in which one or more of the hydrogen atoms are replaced with a halogen radical selected from fluoro, chloro, bromo, and iodo, e.g. trifluoromethyl.

"Cycloalkyl" refers to a fully saturated, monovalent cyclic hydrocarbon radical, having from four to six carbon atoms, such as cyclopentyl and cyclohexyl. Optionally, the cycloalkyl may be substituted with one or more alkyl groups.

"Halocycloalkyl" refers to a cycloalkyl radical, having one or more of its hydrogen atoms replaced by a halogen or haloalkyl, e.g. 4-trifluoromethylcyclohexyl.

"Alkanoic acid radical" refers to a monovalent carboxylic acid radical formed by removal of a hydrogen from the ω-carbon of an acid having from two to four carbon atoms, e.g. acetyl (—CH$_2$COOH), propionyl (—CH$_2$CH$_2$COOH), and butyryl (—CH$_2$CH$_2$CH$_2$COOH).

"Aminoalkanoic acid radical" refers to a monovalent alkanoic acid radical having an amino or mono- or dialkylamino substituent on the α-carbon, e.g. 2-aminopropionyl (—CH$_2$CH(NH$_2$)COOH).

"Alkanoic and aminoalkanoic ester radical" refers to an alkanoic or aminoalkanoic acid radical esterified with a (C$_1$–C$_4$)alkyl, e.g. —CH$_2$COOCH$_3$.

"Alkanoic and aminoalkanoic amide radical" refers to an alkanoic or aminoalkanoic acid radical amidated with NH$_2$ or an alkylamino, e.g. —CH$_2$CONH$_2$.

An "alkylamino" is a group of general formula —NR$^7$R$^8$ wherein at least one of R$^7$ and R$^8$ is an alkyl.

"A bioprecursor of a hydroxy group" is a group which is metabolically converted into hydroxy, such as hydrogen, amino, or an alkyl, aryl, or arylalkyl ester or ether group, e.g. methoxy or O-glucuronide. 4'-Hydroxylation has been reported as an activating step in the metabolism of T$_3$ analogs by Barker and Shimada, *Mayo Clin. Proc.* 39:609–625 (1964) and Jorgensen (supra, pp. 159–162).

"A leaving group" is a chemical grouping which may be displaced from its position in a molecule by a more nucleophilic group. Typical leaving groups include reactive esters, halides, sulfonates, and the like.

"Cholesteremia", also known as cholesterinemia, cholesterolemia, hypercholesteremia, hypercholesterolemia, and hypercholesterinemia, refers to the presence of excessive quantities of cholesterol in the cells and plasma of the circulating blood of mammals. The National Cholesterol Education Program has established a level of 240 mg/dL or higher as indicative of high blood cholesterol in humans.

"Pharmaceutically acceptable salts" refers to those compounds which are formed by reaction of a compound of Formula (I) with a suitable acid or base including: acid addition salts with inorganic acids, such as HCl, HBr, H$_2$SO$_4$, and the like, or with organic acids, such as acetic acid, benzoic acid, and the like; basic addition salts with metal cations, such as Na, K, Mg, Ca, and the like, or with organic cations, such as ethylenediamine; or combinations of both, such as zinc tannate salts.

Preferred Embodiments

Among the compounds of Formula (I) certain embodiments are preferred due to, inter alia, greater efficacy for reducing serum cholesterol levels, improved selectivity, or ease of synthesis.

In a preferred embodiment, the compounds of this invention comprise those of Formula (I) wherein:

R$^1$ is (CH$_2$)$_n$(CHNH$_2$)$_m$C(O)R$^9$; n=1 or 2; m=0 or 1;

R$^3$ and R$^5$ are Cl, Br, or I;

R$^9$ is OH, NH$_2$, or (C$_1$–C$_4$)alkoxy;

R$^{31}$ is H, Cl, Br, I, (C$_1$–C$_4$)alkyl, (C$_4$–C$_6$)cycloalkyl, or —CH$_2$Ar where Ar is selected from 6-hydroxypyridazin-3-yl, 6-methoxypyridazin-3-yl, 6-hydroxypyridazin-3-yl N-oxide, and 6-methoxypyridazin-3-yl N-oxide; R$^{41}$ is OH or (C$_1$–C$_4$)alkoxy; and the pharmaceutically acceptable salts thereof.

More preferred are those compounds of Formula (I) wherein

R$^1$ is an alkanoic or 2-aminoalkanoic acid radical derived from acetic acid, propionic acid, or 2-aminopropionic acid, or the methyl or ethyl ester thereof;

R$^3$ and R$^5$ are both Br or both I;

R$^{31}$ is iodo, isopropyl, cyclopentyl, cyclohexyl, 6-hydroxypyridazin-3-yl, 6-methoxypyridazin-3-yl, 6-hydroxypyridazin-3-yl N-oxide, and 6-methoxypyridazin-3-yl N-oxide; R$^{41}$ is OH, methoxy, or ethoxy; and their pharmaceutically acceptable salts.

Some compounds of Formula (I) may be in the form of a racemic or diastereomeric mixture or as individual isomers or mixtures thereof. For example, compounds of Formula (I) in which R$^1$ is a 2-aminoalkanoic acid may exist as the (R)-isomer, the (S)-isomer, or as a mixture of the (R)- and (S)-isomers. All isomeric forms in resolved and unresolved states are included within the scope of Formula (I).

In addition, it will be appreciated that some of the compounds of Formula (I), such as those in which R$^1$ is an aminoalkanoic acid, may exist as zwitterions under appropriate pH conditions. Similarly, the group Ar may be in a specific zwitterionic or tautomeric form. For example, when Ar is 6-hydroxypyridazin-3-ylmethyl, the tautomeric form 6-oxo-3(1H)-pyridazinylmethyl is included.

Specific examples of compounds of Formula (I) include, but are not limited to:

3,5-dibromo-4-(4-hydroxy-3-iodophenylsulfonyl)phenylacetic acid, 3,5-dibromo-4-(3-iodo-4-methoxyphenylsulfonyl)phenylacetic acid, 3,5-dibromo-4-(4-hydroxy-3-(6-methoxypyridazin-3-ylmethyl)phenylsulfonyl)phenylacetic acid, 3,5-dibromo-4-(3-cyclohexyl-4-hydroxyphenylsulfonyl)phenylacetic acid, 3,5-dibromo-4-(3-cyclohexyl-4-methoxyphenylsulfonyl)phenylacetic acid, 3,5-dibromo-4-(3-cyclopentyl-4-hydroxyphenylsulfonyl)phenylacetic acid, 3-(3,5-dibromo-4-(4-hydroxy-3-isopropylphenylsulfonyl)phenyl)propionic acid, 2-amino-3-(3,5-dibromo-4-(4-hydroxy-3-isopropylphenylsulfonyl)phenyl)propionic acid, 3,5-dibromo-4-(4-hydroxy-(6-hydroxypyridazin-3-ylmethyl)phenylsulfonyl)phenylacetic acid, 3,5-dibromo-4-(4-hydroxy-3-isopropylphenylsulfonyl)-phenylacetic acid, and 3,5-dibromo-4-(3-isopropyl-4-methoxyphenylsulfonyl)-phenylacetic acid.

Synthesis

Referring to Reaction Scheme 1, a generalized process for preparing the 3,5-substituted sulfones of this invention is presented. This process is preferred for those compounds of Formula (I) wherein $R^3$ and $R^5$ are Cl, Br, or $CH_3$ and m=0 and will be illustrated with reference to the preparation of the 3,5-diCl or diBr compounds, although the process is equally applicable to mixed halo, dimethyl, and mixed methyl/halo compounds.

3,5-Halogenation of a p-hydroxyphenylalkanoate yields the 3,5-dihalo compound 1 (R=alkyl; n=1, 2, or 3). Alternatively, a p-hydroxyphenylalkanoic acid may first be halogenated and subsequently esterified to 1. Halogenation may be carried out by the addition of the halogen to a solution of the alkanoic acid or ester at room temperature. The ethyl ester is preferred.

Following the procedure of Newman and Karnes, *J. Org. Chem.* 31, 3980 (1966), treatment of 1 or a salt thereof with N,N-dimethylthiocarbamoyl chloride in the presence of a base, such as sodium hydride, 1,4-diazabicyclo[2.2.2]octane (Dabco TM), etc., gives the corresponding thiocarbamate 2. Pyrolysis of 2 at a temperature of 200° to 250° C. for 0.5 to 4 hours provides the rearrangement product 3. Saponification of 3, for example at reflux for 1 to 30 hours, forms the mercaptophenylalkanoic acid, which may be esterified to afford compound 4 (R=alkyl).

Compound 4 may then be converted to a sulfenyl halide 6 (X=halo), preferably a sulfenyl chloride, in situ, by methods well known to the skilled artisan, e.g. with an excess of a halogenating agent such as an N-halosuccinimide, sulfuryl halide, or halogen, preferably with sulfuryl chloride or chlorine gas, in an inert solvent, such as dichloromethane.

Alternatively, compound 4 may be converted in stepwise fashion to the sulfenyl halide via the disulfide 5 which is optionally isolated and further reacted with additional halogenating agent as above to give 6.

Preferably the sulfenyl halide is prepared in situ and reacted with a 2-substituted anisole 7 ($R^{41}$=OMe) in the presence of a Lewis acid, such as $AlCl_3$, $SnCl_1$, and the like to obtain the thioether 8 ($R^{41}$=OMe). Demethylation of 8, for example with $BBr_3$, yields 9 ($R^{41}$=OH, R=alkyl) which may be accompanied by the free acid 10 ($R^{41}$=OH, R=H) depending upon the work-up procedure used. Generally, quenching the reaction with methanol yields 9, while an aqueous work-up produces the free acid 10 along with 9. Saponification of 9, for example with an aqueous base, such as aqueous sodium hydroxide, gives the acid 10.

In certain cases, the sulfenyl halide 6 may be reacted with a 2-substituted phenol 7 ($R^{41}$=OH) under the conditions described above for the conversion of 6 to 8 to provide the thioether 9 directly. This process is preferred when $R^{31}$ is a bulky substituent, e.g. cycloalkyl.

Oxidation of the thioethers 8, 9, and 10 to the corresponding sulfones 13, 11, and 12 may be effected by methods well known in the art, such as with two or more equivalents of a peracid, e.g. m-chloroperbenzoic acid (m-CPBA), potassium peroxosulfate (Oxone TM), peracetic acid, hydrogen peroxide in acetic acid, and the like.

Saponification of 13 provides compounds 14 wherein R is H. Demethylation of 13, for example with $BBr_3$ as described above, provides compounds of formula 11 and/or 12; or 11 may be saponified to 12. The esters 11 and 13 may be amidated by treatment with ammonia or a suitable alkylamine at 25° C. for about 24 hours. Alternatively, acids 12 and 14 may be amidated directly using an activating agent, such as N,N-dicyclohexylcarbodiimide, or via the acid chloride.

REACTION SCHEME 1

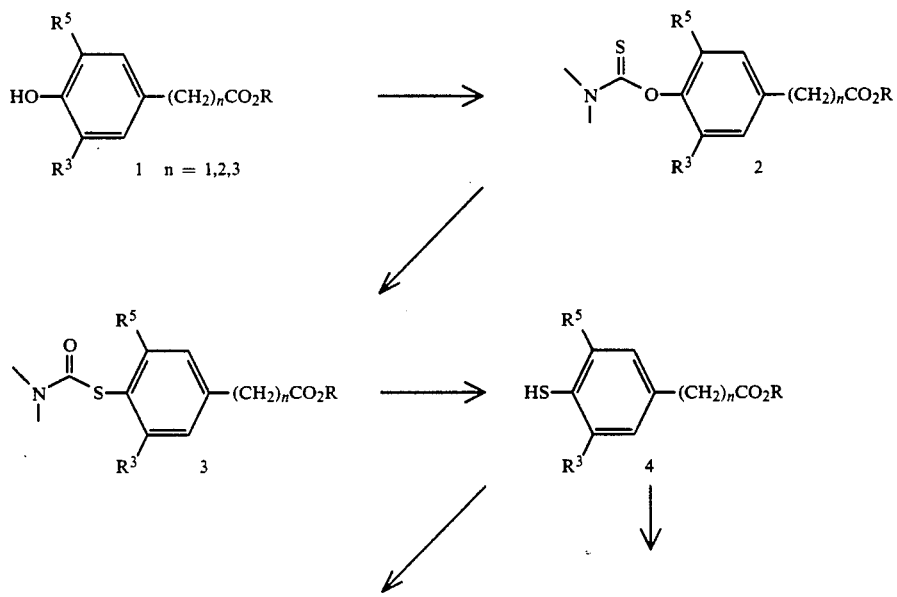

REACTION SCHEME 1
-continued

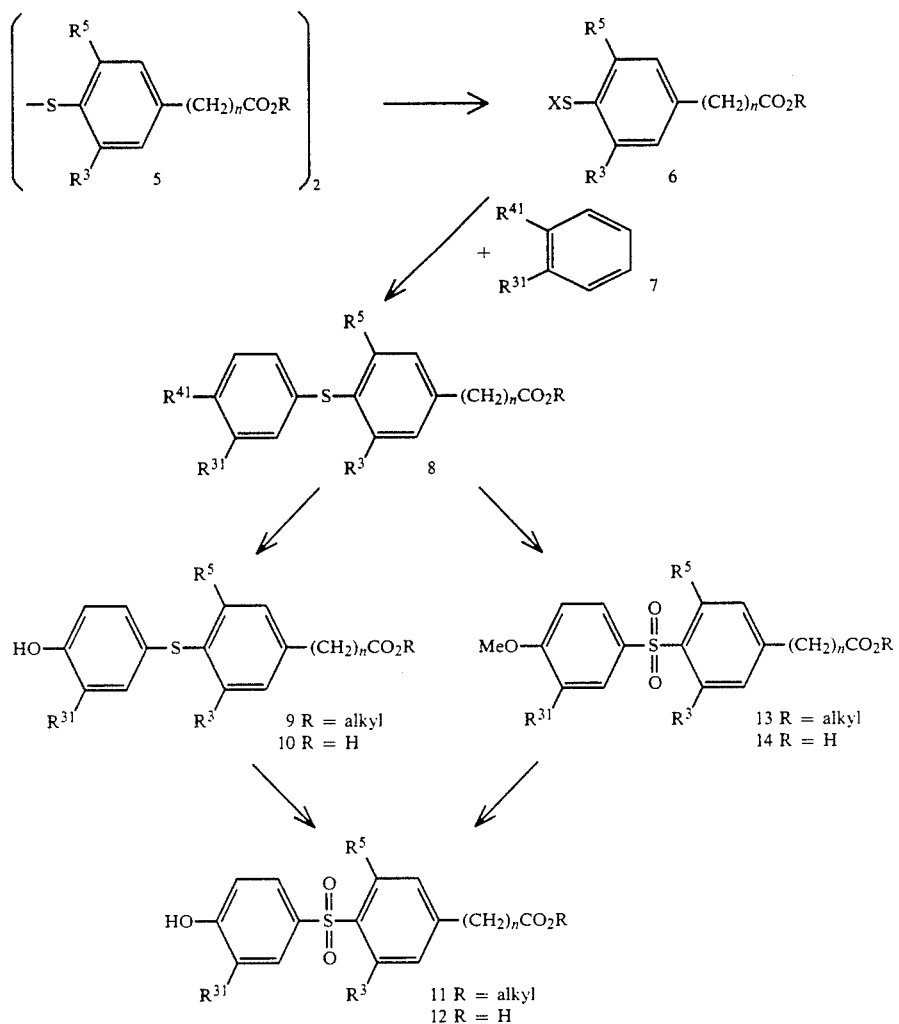

Reaction Scheme 2 presents a generalized process for preparing compounds of the invention in which $R^3$ or $R^5$ is iodo and/or $R^1$ is an aminoalkanoic acid, amide, or ester.

The thioether ester 15 is prepared from the appropriate p-hydroxybenzoic acid or ester and a 2-substituted anisole of formula 7 by a process analogous to that of Reaction Scheme 1 for the synthesis of compound 8. Ester 15 is converted to the alcohol 17 by saponification to the benzoic acid 16 followed by reduction with a suitable reducing agent, for example borane-tetrahydrofuran complex or LiAlH₄ in an ethereal solvent such as tetrahydrofuran. Alternatively, reduction of the ester 15 gives alcohol 17 directly, accompanied by varying amounts of byproduct 17a When $R^3$ or $R^5$ is I. The alcoholic hydroxyl group is then converted to a leaving group X, by methods well known in the art, to give compounds 18 and 18a. Preferably the leaving group is Cl formed by the reaction of 17 with thionyl chloride in dichloromethane, optionally containing catalytic amounts of dimethylformamide.

For the preparation of compounds of Formula (I) wherein $R^1$ is a propionic or aminopropionic acid radical or derivative, compound 18 (or the mixture 18 + 18a) is next reacted with a malonic ester 20 of the formula Z—CH(COOR)₂ wherein Z=H or NR⁷COT, R is alkyl or RR is alkylene, and T is alkyl or haloalkyl, preferably methyl or trifluoro-methyl, in the presence of base, or with a salt of compound 20, preferably the sodium salt, to yield the ester 21. Alternatively, compound 18 is demethylated, as described above for compound 8, to give compound 19. When X is chloro and the dealkylating agent is BBr₃, a mixture of compounds 19 is obtained in which X is Cl/Br. Reaction of compound 19 with the malonic ester 20 as above yields the ester 22.

Oxidation of esters 21 and 22, as described for compounds 8, 9, and 10, gives compounds 23 and 24, respectively. Saponification and decarboxylation of 23 and 24 results in the acids 25 through 2s. Decarboxylation may be achieved by heating the saponified derivatives at or above the melting point, or in one step, by heating the esters 23 and 24 with an inorganic salt, such as an alkali metal halide in wet dimethylsulfoxide. When Z=H, saponification and decarboxylation of esters 23 and 24 produces compounds 25 and 26 having a propionic acid radical at $R^1$. Demethylation of 25 with BBr₃ as described above for compound 18 similarly produces compound 26. When Z=NR⁷COT, removal of the acyl protecting group from compounds 27 and 28, for example, by heating with an aqueous acid, preferably an inorganic acid such as sulfuric acid, produces compounds 29 and 30 having 2-aminopropionic acid radicals at $R^1$. Compound 29 may also be demethylated to compound 30. Reductive alkylation with an $R^8CHO$, such as formaldehyde in the presence of palladized charcoal, may be used to convert the —$NHR^7$ group of 29 and 30 to an —$NR^7R^8$ group.

Compounds of Formula (I) wherein $R^1$ is an acetic acid radical (12 and 14, n=1) may be prepared from compounds 18 and 19 by, for example, treatment with NaCN to replace X with CN, hydrolysis with a strong acid, such as HCl, to convert CN to COOH, and oxidation of the thioether as described above for the oxidation of compound 8. Similarly, the Grignard reagent derived from the reaction of 18 with, for example, Mg in THF, may be carbonated by pouring the Grignard reagent onto crushed dry ice or bubbling $CO_2$ into an ether solution of the Grignard reagent to yield compound 8 (n=1).

It will be apparent to the skilled artisan that the sequence of steps in Reaction Schemes 1 and 2 can be altered, and that compounds of Formula (I) can be converted to other compounds of Formula (I) by alkylation, amidation, dealkylation, esterification, saponification, etc.

REACTION SCHEME 2

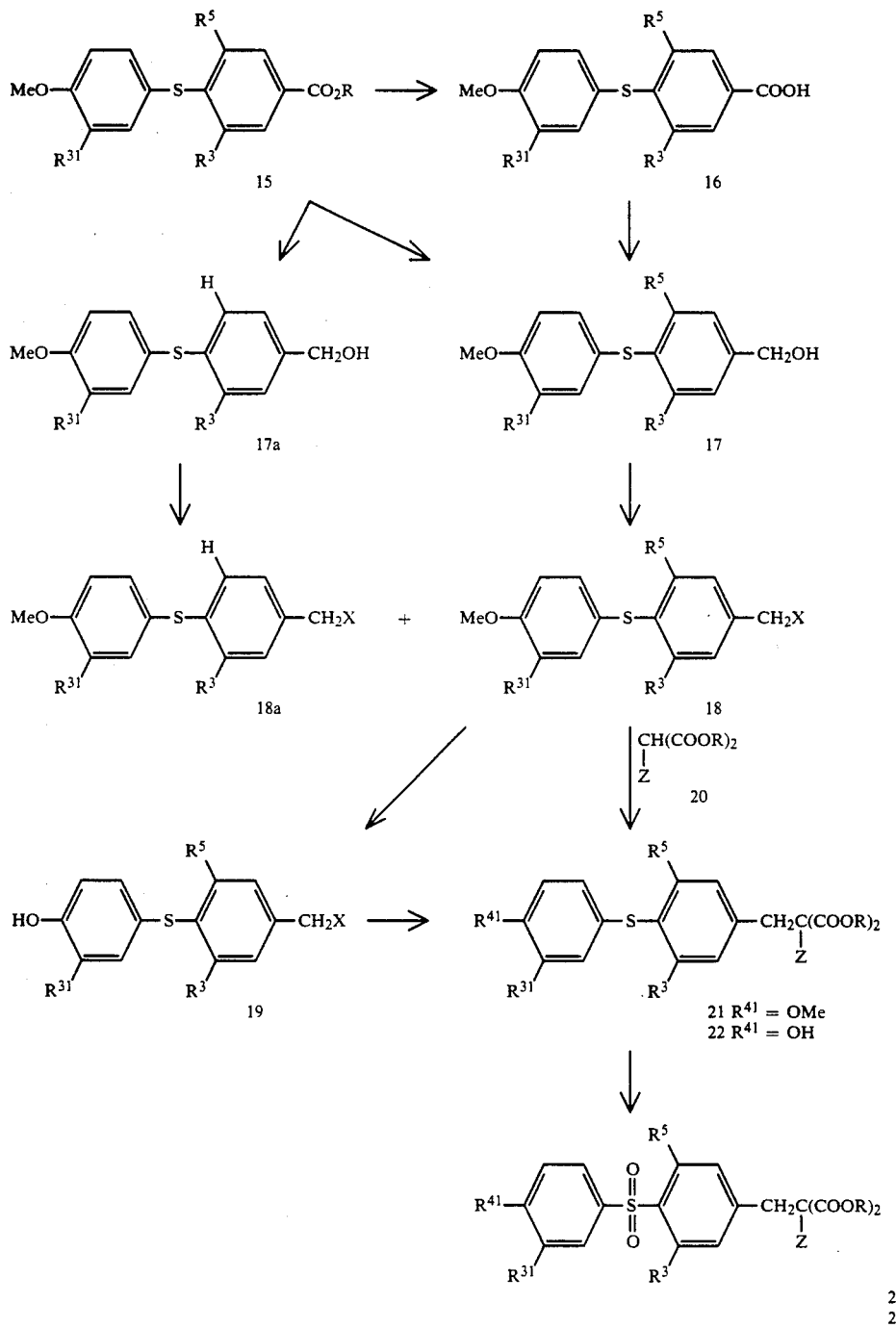

-continued
REACTION SCHEME 2

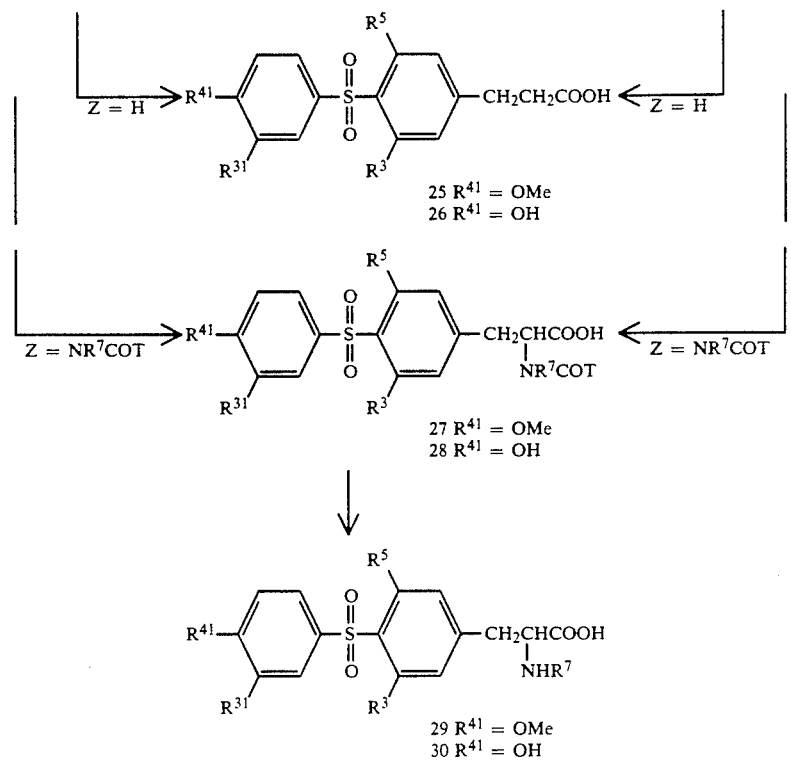

Referring to Reaction Scheme 3, for those embodiments of the invention in which Ar is pyridazinyl (or pyridyl), the intermediate 31 may be prepared as described in European Patent Publication No. 188 351, the disclosure of which is incorporated by reference herein. Intermediate 31 ($R^{41}$=OMe, OH; $R^*$=OH, Cl) may be reacted with compound 6 (R=alkyl), as described in Reaction Scheme 1, substituting 31 for 7, to provide the thioether 32, which may be further processed as described in Reaction Schemes 1 and 2 to obtain the pyridazinyl sulfone 33 (R=H, alkyl; $R^{41}$=OH, OMe; $R^*$=OH) or the pyridazinyl N-oxide sulfone 34 (R=H, alkyl; $R^{41}$=OH, OMe; $R^*$=Cl). In Compound 34, the N-oxide locant may be either of the pyridazinyl nitrogens and is so indicated in Reaction Scheme 3; $R^*$=Cl may be converted to OH or alkoxy, if desired.

REACTION SCHEME 3

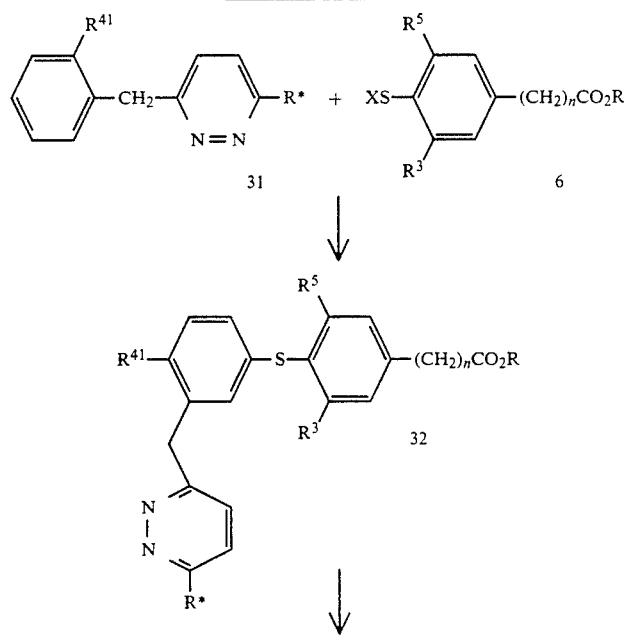

-continued
REACTION SCHEME 3

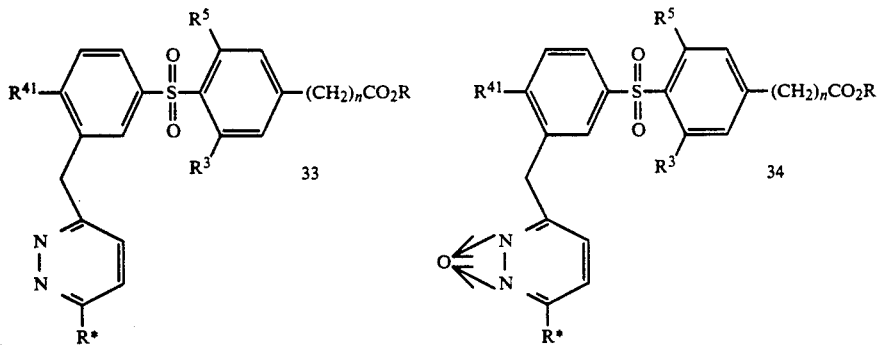

Administration and Utility

Compounds of Formula (I) have been found to exhibit selective thyromimetic activity by lowering serum cholesterol at doses which do not significantly affect cardiac function.

Patients having elevated plasma lipid levels are considered at risk of developing coronary heart disease or other manifestations of atherosclerosis as a result of their high plasma cholesterol and/or triglyceride concentrations. Compounds of this invention are indicated for treatment of disease states characterized by cholesteremia, particularly high LDL (low density lipoprotein) cholesterol.

In addition, compounds of Formula (I) may be indicated in thyroid hormone replacement therapy in patients with compromised cardiac function.

In therapeutic use the compounds of the present invention are usually administered in a standard pharmaceutical composition.

Administration of the compounds of Formula (I), or their pharmaceutically acceptable salts, in pure form or in an appropriate pharmaceutical composition, can be carried out via any of the accepted modes of administration of agents for serving similar utilities. Thus, administration can be, for example, orally, nasally, parenterally, topically, transdermally, or rectally, in the form of solid, semi-solid, lyophilized powder, or liquid dosage forms, such as for example, tablets, lozenges, suppositories, pills, soft elastic and hard gelatin capsules, powders, solutions, suspensions, syrups, emulsions, or aerosols, or the like, preferably in unit dosage forms suitable for administration of precise dosages.

Actual methods of preparing such dosage forms will be apparent to the skilled artisan; for example, see Remington's *Pharmaceutical Sciences*, 18th Ed., (Mack Publishing Company, Easton, Pa., 1990), the disclosure of which is incorporated by reference herein.

Generally, the compounds of Formula (I), and their pharmaceutically acceptable salts, are administered in a therapeutically effective amount which will vary depending upon the individual and the disease state being treated. Typically, a therapeutically effective daily dose is from about 0.1 to about 30 mg/kg of body weight per day of a compound of formula (I), or a pharmaceutically acceptable salt thereof; preferably, from about 0.1 to about 10 mg/kg of body weight per day; and most preferably, from about 1 to about 10 mg/kg of body weight per day. For example, for administration to a 70 kg person, the dosage range would be from about 7 to about 2100 mg per day of a compound of formula (I), or a pharmaceutically acceptable salt thereof; preferably from about 7 to about 700 mg per day, and most preferably from about 70 to about 700 mg per day. Optionally, a bile salt sequestrant, such as cholestyramine, may be included in the formulation.

The compositions may include a conventional pharmaceutical carrier or excipient and a compound of Formula (I) as active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of formula (I), or a pharmaceutically acceptable salt thereof, and 99% to 1% by weight of a suitable pharmaceutical excipient. Preferably, the composition will be about 5% to 75% by weight of a compound(s) of formula (I), or a pharmaceutically acceptable salt thereof, with the rest being suitable pharmaceutical excipients.

A liquid composition will generally consist of a suspension or solution of the compound or pharmaceutically acceptable salt in a suitable liquid carrier(s), for example ethanol, glycerine, sorbitol, a non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example a powder containing active compound, suspending agent, and a sweetener can be reconstituted with water to form a suspension; and a syrup can be prepared from a powder containing active ingredient and a sweetener.

A composition in the form of a tablet can be prepared using any suitable pharmaceutical carrier(s) routinely used for preparing solid compositions. Examples of such carriers include magnesium stearate, starch, lactose, sucrose, mannitol, microcrystalline cellulose and binders, for example polyvinylpyrrolidone and the like. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Compounds of Formula (I) and their pharmaceutically acceptable salts which are active when given parenterally can be formulated for intramuscular or intravenous administration.

A typical composition for intramuscular administration will consist of a suspension of active ingredient in an oil, for example arachis oil or sesame oil. A typical composition for intravenous administration will consist of a sterile isotonic aqueous solution containing, for example active ingredient, dextrose, sodium chloride, a co-solvent, for example polyethylene glycol and, optionally, a chelating agent, for example ethylenediaminetetraacetic acid and an anti-oxidant, for example, sodium metabisulphite. Alternatively, the solution can be freeze dried and then reconstituted with a suitable solvent just prior to administration.

Compounds of Formula (I) and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

Compounds of Formula (I) may be formulated into controlled release compositions for oral or parenteral delivery. Such compositions may take a variety of forms, e.g. liposomal formulations or polymeric microspheres, as taught by Kent et al. in U.S. Pat. No. 4,675,189.

Compounds of Formula (I) and their pharmaceutically acceptable salts which are active on topical administration can be formulated as such or incorporated into a device adapted to provide transdermal delivery. Such devices include, for example, an active compound reservoir or matrix and optionally a penetration enhancer.

If desired, a pharmaceutical composition of the invention may also contain minor amounts of auxiliary substances such as wetting or emulsifying agents, pH buffering agents, antioxidants, and the like, for example, citric acid, sorbitan monolaurate, triethanolamine oleate, and butylated hydroxytoluene.

Assay Procedures

In determining the utility of a compound of this invention for treating cholesteremia, a mouse model assay was used. Male mice (strain C57B1/KsJ db/m; Jackson Laboratory, Bar Harbor, Ma.), weighing 23 to 35 g, 6 to 8 weeks at delivery, 8 to 20 weeks at the beginning of the experiment, were housed 10 per cage, subjected to a 12 hour light-dark cycle beginning at 6 A.M. The mice were fed ad libitum with Purina Rodent Chow (Purina #15001) and water ad libitum until the initial baseline bleed. Then, the mice were either maintained on a normal diet or given a special high fat/high cholesterol diet (Teklad #186257, Wayne Laboratory Animal Diets, Madison, Wis.), pelleted at ¼". After a 1-3 week lead-in on the high fat diet another bleed was done to establish a high fat baseline, against which drug treatments were compared.

Mice were ear-tagged with individual identification numbers, assigned to experimental groups consisting of 10 mice each, and their weights recorded. Baseline bleeds at the start of the experiment were obtained from the retro-orbital sinus, using glass capillary tubes, under 60% $CO_2$/40% $O_2$ anesthesia. 200 Microliters of blood were taken at baseline and subsequent bleeds, except the final bleed, where 400 microliters were obtained. Blood was transferred to serum separator tubes (Becton-Dickinson #15690) and serum was separated from formed blood elements by centrifugation (12,000 xg, 1 minute) and stored in plastic tubes at $-70°$ C. until analysis for lipids. Drug was either given by gavage twice daily using 10 μL of vehicle per gram body weight each time or was provided in the feed ad libitum.

Treatments by gavage were in the early morning and mid-afternoon. For gavage studies the highest dose of each drug was dissolved at 50 to 100X concentration in 1M NaOH followed by dilution to 1X using isotonic saline. Subsequent dilutions were made in 0.01M NaOH in isotonic saline.

Drugs given in the feed were prepared in NaOH/ethanol. The drug was first dissolved in 100 μL of 1M NaOH and this solution was added to approximately 30 mL of ethanol. After mixing with the feed at 10-fold drug excess, excess ethanol was evaporated. This 10X stock supply was mixed with 9 parts of feed, using a food blender, and stored at $-20°$ C. until use. The mice were given unlimited access to the feed. Mice eat approximately 1/10 of their body weight per day. Therefore, the drug was prepared at a final dosage level in the feed which was 10X the desired daily dose based on body weight.

Heart weights were used to assess cardiac hypertrophy due to drug-induced cardiac stimulation. Hearts were trimmed of excess fat, rinsed in saline, carefully blotted dry and immediately weighed to the nearest 0.01 or 0.001 gram.

Serum cholesterol and high density lipoprotein-cholesterol (HDL-C) were measured according to the following published methods, the disclosures of which are incorporated by reference herein:

Total cholesterol was determined by an enzymatic, colorimetric procedure, according to Allain et al., *Clin. Chem* 20, 470 (1974), at a test wavelength of 510 nanometers.

HDL particles were separated from low density lipoprotein (LDL) and very low density lipoprotein (VLDL) particles using phosphotungstic acid and magnesium chloride precipitation of (LDL+VLDL) according to Marz et al., *Clin. Chim. Acta* 160, 1 (1986), and Assman et al., *Clin. Chem.* 29, 2026 (1983), using Sigma Diagnostics Procedure 352-4. HDL-C was measured using the same method as that used for total cholesterol. (LDL+VLDL)-cholesterol was determined by calculation, subtracting HDL-C from total cholesterol.

All procedures were modified, by reducing reagent volumes, to run in microtiter plates. A Molecular Devices Vmax plate reader were used to measure absorbances. Statistical significance was determined by analysis of variance (ANOVA), using the SAS General Linear Model statistical program for personal computers (version 6.04).

The following specific Examples are intended to illustrate the synthesis of representative compounds of the invention and should not be construed as limiting the scope of the claims in any way. All reagents were purchased from commercial sources, e.g. Aldrich Chemical Co., and were used without further purification.

Preparation A

3,5-Dibromo-4-hydroxyphenylacetic acid

Bromine (210 g, 1.31 mol) was added over about one hour to a vigorously stirred solution of 4-hydroxyphenylacetic acid (100 g, 0.65 mol) in 500 mL of acetic acid. The reaction was allowed to proceed for 18 hrs and then quenched with water. The solid product was collected by filtration, washed with water, and dried in a vacuum oven to obtain 3,5-dibromo-4-hydroxyphenylacetic acid (160 g, 0.51 mol, 78% yield).

Preparation B

Ethyl 3,5-dibromo-4-hydroxyphenylacetate 3,5-Dibromo-4-hydroxyphenylacetic acid (60 g, 0.19 mol), from Preparation A, was suspended in 1 L of ethanol and 10 mL of concentrated sulfuric acid and heated at reflux overnight. The reaction mixture was cooled, concentrated and the product collected by filtration, washed with water, and dried in a vacuum oven to obtain ethyl 3,5-dibromo-4-hydroxyphenylacetate.

Preparation C

Ethyl 3,5-dibromo-4-(N,N-dimethylthiocarbamoyloxy)phenylacetate

Following the procedure of Newman and Karnes, *J. Org. Chem.* 31, 3980 (1966), a mixture of ethyl 3,5-dibromo-4-hydroxyphenylacetate (20 g, 0.06 mol), from Preparation B, N,N-dimethylthiocarbamoyl chloride (10.9 g, 0.088 mol), and 1,4-diazabicyclo[2.2.2]octane (Dabco TM) (13.4 g, 0.12 mol) in 250 mL DMF was heated, with stirring, at 70° C. for one hour. The reaction mixture was cooled and the precipitate (Dabco-HCl salt) removed by filtration and washed well with ethyl acetate. The filtrate was concentrated on a rotary evaporator and the solid collected by filtration, washed well with water and dried in vacuum to obtain ethyl 3,5-dibromo-4-(N,N-dimethylthiocarbamoyloxy)phenylacetate (16 g, 0.037 mol, 62% yield), MP: 93°–95° C. (hexane/ethyl acetate).

$C_{13}H_{15}Br_2NO_3S$ Calc'd: C 36.72, H 3.55, N 3.29. Found: C 36.92, H 3.57, N 3.28.

Preparation D

Ethyl 3,5-dibromo-4-(N,N-dimethylcarbamoylthio)phenylacetate

Ethyl 3,5-dibromo-4-(N,N-dimethylthiocarbamoyloxy)phenylacetate (15 g, 0.035 mol), from Preparation C, was heated at 230° C. under $N_2$ for 0.5 hr. The melt was cooled and purified by flash chromatography (silica gel, 230–400 mesh, 50:45:5 hexane:dichloromethane:acetone) to obtain ethyl 3,5-dibromo-4-(N,N-dimethylcarbamoylthio)phenylacetate (8 g, 0.019 mol), MP: 105°–107° C. (hexane/ethyl acetate).

$C_{13}H_{15}Br_2NO_3S$ Calc'd: C 36.92, H 3.55, N 3.29. Found: C 37.53, H 3.42, N 3.10.

Preparation E

Methyl 3,5-dibromo-4-mercaptophenylacetate

A solution of ethyl 3,5-dibromo-4-(N,N-dimethylcarbamoylthio)phenylacetate (8 g, 0.018 mol), from Preparation D, in 100 mL of 10% aqueous sodium hydroxide and 10 mL ethanol was heated at reflux for 20 hrs under a nitrogen atmosphere. The reaction mixture was cooled and neutral impurities extracted with ethyl acetate. The aqueous phase was acidified with 6N HCl and extracted twice with ethyl acetate. The combined extracts were washed with water and saturated sodium chloride solution, dried ($Na_2SO_4$), and the solvent removed on a rotary evaporator. The residue was dissolved in methanol and treated with 3 mL of concentrated sulfuric acid and heated at reflux temperature for 3 hrs. The reaction mixture was cooled and concentrated. The residue was diluted with ethyl acetate, washed with water and brine, dried ($Na_2SO_4$), and the solvent removed on a rotary evaporator. The residue was purified by flash chromatography (silica gel, 5% acetone/hexane) to obtain methyl 3,5-dibromo-4-mercaptophenylacetate (3.5 g, 0.01 mol, 57% yield), MP: 63.5°–65° C.

$C_9H_9Br_2O_2S$ Calc'd: C 31.79, H 2.37. Found: C 32.12, H 2.24.

EXAMPLE 1

(a) Methyl 3,5-dibromo-4-(3-isopropyl-4-methoxyphenylthio)phenylacetate

Sulfuryl chloride (0.9 mL, 0.011 mol) in 5 mL of dichloromethane was added dropwise to a solution of methyl 3,5-dibromo-4-mercaptophenylacetate (3.4 g, 0.11 mol), from Preparation E, in 50 mL dichloromethane. The pale yellow solution was allowed to stand for 1 hour and transferred to an addition funnel. The resulting sulfenyl chloride was then added dropwise to an ice-cooled suspension of 2-isopropylanisole (1.8 g, 0.022 mol) and aluminum chloride (2.8 g, 0.02 mol) in methanol. The reaction mixture was allowed to warm to room temperature and stirred for an additional 15 min. The reaction mixture was then poured on to ice water and extracted twice with dichloromethane. The combined extract was washed with water and brine, dried ($Na_2SO_4$), and evaporated on a rotary evaporator. The residue was purified by flash chromatography (silica gel, 5:1 acetone:hexane) to obtain methyl 3,5-dibromo-4-(3-isopropyl-4-methoxyphenylthio)-phenylacetate (3.5 g, 0.007 mol, 70% yield), MP: 73°–76° C.

$C_{19}H_{20}Br_2O_3S$ Calc'd: C 46.74, H 4.12. Found: C 47.05, H 4.13.

(b) Methyl 3,5-dibromo-4-(3-isopropyl-4-methoxyphenylsulfonyl)-phenylacetate A mixture of methyl 3,5-dibromo-4-(3-isopropyl-4-methoxyphenylthio)phenylacetate (3.5 g, 0.007 mol) from Example 1(a) and 50 % m-chloroperbenzoic acid (m-CPBA) (6.2 g, 0.017 mol) in $CH_2Cl_2$ was allowed to react for 20 hrs. Excess m-CPBA was removed by treatment with aqueous sodium bisulfite. The organic layer was separated and washed with sodium carbonate solution, water and brine, and dried ($Na_2SO_4$). After removal of the solvent on a rotary evaporator, the product was crystallized from hexane-ethyl acetate mixture to obtain the sulfone, methyl 3,5-dibromo-4-(3-isopropyl-4-methoxyphenylsulfonyl)phenylacetate (3.5 g, 0.0067 mol, 95% yield), MP: 105°–106° C.

$C_{19}H_{20}Br_2O_5S$ Calc'd: C 43.86, H 3.87. Found: C 44.15, H 3.93.

EXAMPLE 2

Methyl 3,5-dibromo-4-(4-hydroxy-3-isopropylphenylsulfonyl)-phenylacetate

A 1M solution of boron tribromide (17 mL, 0.017 mol) in dichloromethane was added to an ice-cooled solution of methyl 3,5-dibromo-4-(3-isopropyl-4-methoxyphenylsulfonyl)phenylacetate (3.5 g, 0.0067 mol), from Example 1, in dichloromethane. The mixture was warmed to room temperature and allowed to react for 3 hrs. Excess boron tribromide was quenched by the addition of methanol to the ice-cooled reaction mixture and the reaction mixture was concentrated on a rotary evaporator. The residue was dissolved in ethyl acetate, washed with water and brine, and dried ($Na_2SO_4$). The residue obtained after removal of the solvent was purified by flash chromatography (silica gel, 45:45:10 hexane:$CH_2Cl_2$: acetone) to obtain methyl 3,5-dibromo-4-(4-hydroxy-3-isopropylphenylsulfonyl)phenylacetate (2.9 g, 0.0057 mol, 85% yield). MP: 159°–160° C. (hexane/ethyl acetate).

$C_{18}H_{28}Br_2O_5S \cdot \frac{1}{2}H_2O$ Calc'd: C 41 96, H 3.52. Found: C 41.98, H 3.58.

EXAMPLE 3

3,5-Dibromo-4-(4-hydroxy-3-isopropylphenylsulfonyl)-phenylacetic acid

A suspension of methyl 3,5-dibromo-4-(4-hydroxy-3-isopropylphenylsulfonyl)phenylacetate (2.7 g, 0.0053 mol), from Example 2, in 30 mL sodium hydroxide (5%) was heated at 60° C. for 10 min. The reaction mixture was cooled and extracted with ethyl acetate. The aqueous phase was acidified with hydrochloric acid (6N) and extracted with ethyl acetate (2X). The combined extract was washed with water and brine and dried ($Na_2SO_4$). The residue obtained after removal of the solvent was crystallized from hexane-ethyl acetate to obtain 3,5-dibromo-4-(4-hydroxy-3-isopropylphenylsulfonyl)phenylacetic acid (2.5 g, 0.0051 mol, 96% yield), MP: 171°–172° C.

$C_{17}H_{16}Br_2O_5S$ Calc'd: C 41.48, H 3.27. Found: C 41.58, H 3.31.

EXAMPLE 4

3,5-Dibromo-4-(3-isopropyl-4-methoxyphenylsulfonyl)-phenylacetic acid

Methyl 3,5-dibromo-4-(3-isopropyl-4-methoxyphenylsulfonyl)phenylacetate (0.6 g), prepared by the method of Example 1, was treated with KOH in 10% aqueous MeOH for 0.5 hour, acidified and the product collected by filtration, washed with water, and dried in a vacuum oven to yield 3,5-dibromo-4-(3-isopropyl-4-methoxyphenylsulfonyl)phenylacetic acid. MP 170°–173° C.

$C_{18}H_{18}Br_2O_5S$ Calc'd: C 42.71, H 3.58. Found: C 42.57, H 3.66.

EXAMPLE 5

3,5-Dibromo-4-(3-cyclopentyl-4-hydroxyphenylsulfonyl)phenylacetic acid

Sulfuryl chloride (0.5 mL) was added dropwise to a solution of methyl 3,5-dibromo-4-mercaptophenylacetate (Preparation E, 0.8 g) in 50 mL of dichloromethane for 1 hour. The sulfenyl chloride product was then added dropwise to an ice-cooled suspension of 2-cyclopentylphenol (0.44 g) and tin (IV) chloride (0.53 mL) in methanol. Following the procedures of Examples 1 and 3, the product methyl 3,5-dibromo-4-(3-cyclopentyl-4-hydroxyphenylsulfonyl)phenylacetate, MP: 171°–173.5° C., (0.7 g) was purified and converted to 3,5-dibromo-4-(3-cyclopentyl-4-hydroxyphenylsulfonyl)phenylacetic acid, MP: 196°–198° C.

$C_{19}H_{18}Br_2O_5S$ Calc'd: C 44.03, H 3.50. Found: C44.31, H 3.51.

EXAMPLE 6

3,5-Dibromo-4-(3-cyclohexyl-4-hydroxyphenylsulfonyl)phenylacetic acid

Following the procedures of Examples 1 and 3, methyl 3,5-dibromo-4-mercaptophenylacetate (0.44 g) was reacted with 2-cyclohexylphenol (0.25 g) to form the thioether (0.4 g) which was oxidized to the sulfone (0.3 g) and then converted to 3,5-dibromo-4-(3-cyclohexyl-4-hydroxyphenylsulfonyl)phenylacetic acid (0.27 g), using 1N KOH/EtOH and HCl (conc), MP: 226°–230° C.

$C_{20}H_{20}Br_2O_5S$ Calc'd: C 45.13, H 3.78. Found: C 45.12, H 3.93.

EXAMPLE 7

3,5-Dibromo-4-(3-cyclohexyl-4-methoxyphenylsulfonyl)phenylacetic acid

Following the procedure of Example 1, 2-cyclohexylanisole (0.3 g) and methyl 3,5-dibromo-4-mercaptophenylacetate (0.5 g) were reacted to yield the thioether (0.66 g) which was then converted to methyl 3,5-dibromo-4-(3-cyclohexyl-4-methoxyphenylsulfonyl)-phenylacetate (0.55 g), MP: 147°–154° C.

$C_{22}H_{24}Br_2O_5S$ Calc'd: C 47.15, H 4.31. Found: C 47.02, H 4.35.

Hydrolysis of the ester, following the procedure of Example 3, gave 3,5-dibromo-4-(3-cyclohexyl-4-methoxyphenylsulfonyl)phenylacetic acid, recrystallized from hexane/ethyl acetate, MP: 146°–150.5° C.

$C_{21}H_{22}Br_2O_5S$ Calc'd: C 46.17, H 4.06. Found: C 46.80, H 4.34.

EXAMPLE 8

3,5-Dibromo-4-(4-hydroxy-3-(4-hydroxybenzyl)phenylsulfonyl)phenylacetic acid Following the procedures of Examples 1 to 3, methyl 3,5-dibromo-4-mercaptophenylacetate (4 g) was reacted with 2-(4-methoxybenzyl)anisole (2.6 g) to yield the thioether (2.2 g) which was converted to 3,5-dibromo-4-(4-hydroxy-3-(4-hydroxybenzyl)phenylsulfonyl)-phenylacetic acid and recrystallized from ethyl acetate/hexane, MP: 113°–115.5° C.

$C_{21}H_{16}Br_2O_6S \cdot 0.2$ EtOAc Calc'd: C 45.88, H 3.11. Found: C 46.05, H 3.11.

EXAMPLE 9

3,5-Dibromo-4-(4-hydroxy-1-naphthylsulfonyl)-phenylacetic acid

Following the procedures of Examples 1 to 3, methyl 3,5-dibromo-4-mercaptophenylacetate (2 g) was reacted with 1-methoxynaphthalene (1.4 g) to form the thioether, which was converted to 3,5-dibromo-4-(4-hydroxy-1-naphthylsulfonyl)phenylacetic acid, MP: 199°–203° C.

$C_{18}H_{12}Br_2O_5S$ Calc'd: C43.22, H 2.42. Found: C 43.50, H 2.49.

EXAMPLE 10 acid

Following the procedures of Example 1, but substituting 2-iodoanisole for 2-isopropylanisole, methyl 3,5-dibromo-4-mercaptophenylacetate (1 g) was reacted with 2-iodoanisole (0.7 g) to yield the thioether, methyl 3,5-dibromo-4-(3-iodo-4-methoxyphenylthio)phenylacetate (1.4 g) which in turn was oxidized to methyl 3,5-dibromo-4-(3-iodo-4-methoxyphenylsulfonyl)phenylacetate, MP: 127°–129° C. The acetate was saponified to the acid, 3,5-dibromo-4-(3-iodo-4-methoxyphenylsulfonyl)phenylacetic acid, MP: 158°–162° C.

$C_{15}H_{11}Br_2IO_5S$ Calc'd: C 30.53, H 1.87. Found: C 30.82, H 1.79.

EXAMPLE 11

3,5-Dibromo-4-(4-hydroxy-3-iodophenylsulfonyl)phenylacetic acid

Following the procedures of Examples 1 to 3, the thioether of Example 10 was converted to methyl 3,5-dibromo-4-(4-hydroxy-3-iodophenylsulfonyl)phenylacetate. MP: 174°–176° C. The acetate was saponified to the acid, 3,5-dibromo-4-(4-hydroxy-3-iodophenylsulfonyl)phenylacetic acid. MP: foam.

$C_{14}H_9Br_2IO_5S$ Calc'd: C 29.19, H 1.59. Found: C 29.32, H 1.50.

EXAMPLE 12

3,5-dibromo-4-(4-hydroxy-3-(6-methoxypyridazin-3-ylmethyl)phenylsulfonyl)phenylacetic acid N-oxide Following the procedures of Examples 1a and 2, methyl 3,5-dibromo-4-mercaptophenylacetate (1.3 g) was reacted with 2-(6-chloropyridazin-3-ylmethyl)anisole (0.8 g), prepared as in Example 33 of European Patent Publication No. 0 188 351, to yield the thioether methyl 3,5-dibromo-4-(3-(6-chloropyridazin-3-ylmethyl)-4-methoxyphenylthio)phenylacetate.

The thioether was then demethylated following the procedure of Example 2 to give methyl 3,5-dibromo-4-(3-(6-chloropyridazin-3-ylmethyl)-4-hydroxyphenylthio)phenylacetate, MP: 133°–135° C., and oxidized following the procedure of Example 1b to methyl 3,5-dibromo-4-(3-(6-chloropyridazin-3-ylmethyl)-4-hydroxyphenylsulfonyl)phenylacetate N-oxide (0.55 g), MP: 148°–150° C., which upon saponification with 1.2N NaOH solution in ice cold aqueous methanol gave 3,5-dibromo-4-(4-hydroxy-3-(6-methoxypyridazin-3-ylmethyl)phenylsulfonyl)phenylacetic acid N-oxide. MP: 198°–200° C.

$C_{20}H_{16}I_4Br_2N_2O_7S$ Calc'd: C 40.83, H 2.74, N 4.76. Found: C 40.80, H 2.70, N 4.70.

EXAMPLE 13

3,5-Dibromo-4-(4-hydroxy-3-(6-hydroxypyridazin-3-ylmethyl)phenylsulfonyl)phenylacetic acid Following the procedures of Examples 1 to 3, methyl 3,5-dibromo-4-mercaptophenylacetate (1.2 g) was reacted with 2-(6-hydroxypyridazin-3-ylmethyl)anisole (0.75 g) to yield the thioether which was oxidized to methyl 3,5-dibromo-4-(3-(6-hydroxypyridazin-3-ylmethyl)-4-methoxyphenylsulfonyl)phenylacetate, MP: 208°–209° C., and then demethylated and saponified to 3,5-dibromo-4-(4-hydroxy-3-(6-hydroxypyridazin-3-ylmethyl)phenylsulfonyl)phenylacetic acid, MP: 160°–162° C.

$C_{19}H_{14}N_2Br_2O_6S \cdot H_2O$ Calc'd: C 39.60, H 2.80, N 4.86. Found: C 39.60, H 2.57, N 4.93.

EXAMPLE 14

3-(3,5-Dibromo-4-(4-hydroxy-3-isopropylphenylsulfonyl)phenyl)propionic acid Methyl 3,5-dibromo-4-(3-isopropyl-4-methoxyphenylthio)benzoate (2.3 g), prepared analogously to Procedures A through E and Example 1(a), from 3,5-dibromo-4-hydroxybenzoic acid and 2-isopropylanisole, was reduced with lithium aluminum hydride (1M in THF, 5 mL) at 0° C. to yield a mixture of the 3,5-dibromo and 5-desbromo thiobenzyl alcohols. The mixture of alcohols in turn was converted to a mixture of thiobenzyl chlorides using SOCl$_2$ (1.75 mL) in dichloromethane (50 mL) containing 0.1 mL of dimethyl formamide.

Diethyl malonate (1.0 g, 0.006 eq) was added to a solution of sodium ethoxide, prepared by dissolving sodium (0.14 g, 0.006 eq) in ethanol, and the mixture stirred for five minutes. The 3,5-dibromo-4-(3-isopropyl-4-methoxyphenylthio)benzyl chloride (0.94 g) with the accompanying 5-desbromo impurity in THF was added to the diethyl malonate solution and the resulting mixture allowed to react until all the thiobenzyl chloride was converted to the diethyl thiobenzylmalonate (about 5 hrs). The mixture was poured into water, extracted with ethyl acetate, and the residue used without further purification.

The diethyl thiobenzylmalonate was saponified with NaOH (10 eq) in 50% aqueous methanol to the thiobenzylmalonic acid, which was re-esterified with H$_2$SO$_4$ in methanol to provide dimethyl 3,5-dibromo-4-(3-isopropyl-4-methoxyphenylthio)benzylmalonate. The product was purified by flash chromatography (silica gel, acetone/CH$_2$Cl$_2$/hexane, 50/25/25) to remove the 5-desbromo impurity.

To 0.3 g of the dimethyl thiobenzylmalonate was added m-CPBA (0.28 g) in dichloromethane; the solution was stirred for 72 hours, concentrated, diluted with ethyl acetate, extracted with sodium bicarbonate, and purified by flash chromatography (silica gel, acetone/CH$_2$Cl$_2$/hexane, 50/25/25) to yield 0.3 g of dimethyl 3,5-dibromo-4-(3-isopropyl-4-methoxyphenylsulfonyl)benzylmalonate, MP: 121°–123° C.

The dimethyl sulfonylbenzylmalonate (0.3 g) was stirred with a 1M solution of BBr$_3$ in CH$_2$Cl$_2$ (2 mL) overnight, the solvent evaporated, and the residue treated with 2N NaOH overnight at room temperature and then acidified with HCl (conc). 5 mL of dioxane was added and the solution heated at 80° C. for 24 hours. The product was extracted with ethyl acetate and purified by flash chromatography (silica gel, acetone/CH$_2$Cl$_2$/acetic acid, 90/10/1) to yield 0.2 g of 3-(3,5-dibromo-4-(4-hydroxy-3-isopropylphenylsulfonyl)phenyl)propionic acid, MP: 186°–188° C.

EXAMPLE 15

2-amino-3-(3,5-dibromo-4-(4-hydroxy-3-isopropylphenylsulfonyl)phenyl)propionic acid Sodium (0.48 g) was added to 50 mL ethanol; after all the sodium dissolved, diethyl acetamidomalonate (4.67 g) was added. The resulting slurry was allowed to stir for 15 minutes and 3,5-dibromo-4-(3-isopropyl-4-methoxyphenylthio)benzyl chloride (2.09 g), prepared as in Example 14, in THF was added. The resulting mixture was heated at 70° C. for 24 hours, cooled, extracted with ethyl acetate, washed with water and brine, dried, concentrated, and purified by flash chromatography (silica gel, $CH_2Cl_2$/hexane/ethyl acetate, 40/58/2) to yield 0.9 g of diethyl 3,5-dibromo-4-(3-isopropyl-4-methoxyphenylthio)benzylacetamidomalonate, MP: 117°–118.5° C., (hexane/ethyl acetate).

$C_{26}H_{32}Br_2NO_6S$ Calc'd: C 48.3, H 4.98, N 2.16. Found: C 48.7, H 4.94, N 1.57.

The thiobenzylacetamidomalonate (1.0 g) was stirred with m-CPBA (0.67 g) in $CH_2Cl_2$ at room temperature overnight. The product was stirred with 20% $NaHSO_3$, followed by aqueous potassium carbonate. The organic layer was washed with water and brine, dried and purified by flash chromatography (silica gel, hexane/$CH_2Cl_2$/acetone, 50/45/5) to yield diethyl 3,5-dibromo-4-(3-isopropyl-4-methoxyphenylsulfonyl)benzylacetamidomalonate (1 0 g), MP: 164°–168° C.

$C_{26}H_{31}Br_2NO_8S$ Calc'd: C 46.09, H 4.61, N 2.06. Found: C 46.32, H 4.76, N 1.71.

The sulfonylbenzylacetamidomalonate (1.0 g) was dissolved in aqueous KOH (0.4 g). The solution was cooled and acidified with HCl until precipitation was complete. The mixture was heated at 90° C. for one hour, cooled, the solid collected by filtration, and dried in a vacuum oven at 50° C. overnight to yield 3,5-dibromo-4-(3-isopropyl-4-methoxyphenylsulfonyl)benzylacetamidomalonic acid (0.675 g).

The 4-methoxyacetamidomalonic acid (0.65 g) was treated with 1M $BBr_3$ in $CH_2Cl_2$ overnight (5 mL) to provide the 4-hydroxyacetamidomalonic acid. The reaction mixture was poured into water. The solid was collected by filtration, washed with water, and dried. The solid was then suspended in 6N HCl (10 mL) and HOAc (5 mL) and heated at 90° C. for three days. The reaction mixture was cooled, concentrated, and dissolved in ethanol, then heated with 1N KOH, extracted with water and brine, and dried with sodium sulfate. The solid was collected by filtration to give 2-amino-3-(3,5-dibromo-4-(4-hydroxy-3-isopropylphenylsulfonyl)-phenyl)propionic acid, MP: 210°–217° C.

$C_{18}H_{15}Br_2NO_5S$ Calc'd: C 41.87, H 3.67, N 2.68. Found: C 41.01, H 3.87, N 2.56.

EXAMPLE 16

This Example illustrates the preparation of a representative pharmaceutical capsule formulation for oral administration containing a compound of Formula (I), or a pharmaceutically acceptable salt thereof, e.g. 3,5-dibromo-4-(4-hydroxy-3-(6-methoxypyridazin-3-ylmethyl)phenylsulfonyl)phenylacetic acid.

| Ingredients | |
|---|---|
| Compound of Formula (I) | 200 mg |
| Lactose, spray-dried | 148 mg |
| Magnesium stearate | 2 mg |

The above ingredients are mixed and introduced into a 30 hard-shell gelatin capsule. Alternatively, the mixture may be introduced into a soft elastic capsule.

EXAMPLE 17

This Example illustrates the preparation of a representative pharmaceutical formulation for injection containing a compound of Formula (I), or a pharmaceutically acceptable salt thereof, e.g. 3,5-dibromo-4-(3-cyclohexyl-4-hydroxyphenylsulfonyl)phenylacetic acid.

| Ingredients | |
|---|---|
| Compound of Formula (I) | 50 mg |
| Mannitol | 2 g |
| HCl (1N) | q.s. to pH 3 |
| Water | q.s. to 100 mL |

EXAMPLE 18

This Example illustrates the preparation of a representative pharmaceutical formulation for rectal administration containing a compound of Formula (I), or a pharmaceutically acceptable salt thereof, e.g. 3-(3,5-dibromo-(4-hydroxy-3-isopropylphenylsulfonyl)-phenyl)propionic acid.

A suppository totalling 2.5 grams is prepared having the following composition:

| Compound of Formula (I) | 700 mg |
|---|---|
| Witepsol H-15* | balance |

(*triglycerides of saturated vegetable fatty acid; Riches-Nelson, Inc., New York, N.Y.).

EXAMPLE 19

A syrup formulation may be prepared from a compound of Formula (I), or a pharmaceutically acceptable salt thereof, e.g. 2-amino-3-(3,5-dibromo-(4-hydroxy-3-isopropylphenylsulfonyl)phenyl)propionic acid, using the following ingredients,

| Ingredients | |
|---|---|
| Compound of Formula (I) | 100 mg |
| Propylene glycol | 10 g |
| Methyl parahydroxybenzoate | 0.1 g |
| Propyl parahydroxybenzoate | 20 mg |
| Sorbitol solution (70% w:v) | 20 mL |
| Flavors | 0.5 mg |
| Saccharin Sodium | 5.0 mg |
| Water | q.s. to 100 mL | by dissolving the active ingredient and preservatives in the propylene glycol, adding the sorbitol, flavors, and sweeteners, mixing, and adjusting the volume to 100 mL with water.

EXAMPLE 20

A solution for injection (0.5 mg/mL) may be prepared from a compound of Formula (I), or a pharmaceutically acceptable salt thereof, e.g. 3,5-dibromo-(4-hydroxy-3-isopropylphenylsulfonyl)phenylacetic acid.

| Ingredients | |
|---|---|
| Compound of Formula (I) | 50 mg |
| Sodium hydroxide (0.1N) | 4 mL |
| Hydrochloric acid (0.1N) | to pH 10 |
| Sodium chloride | 0.9 g |
| Water | to 100 mL |

The active ingredient is dissolved in the sodium hydroxide, the volume adjusted to 80–90 mL with water and the pH adjusted to 10 by dropwise addition of the hydrochloric acid. The sodium chloride is added, the volume adjusted to 100 mL with water and the filtered solution filled into ampoules or vials. The final product can be sterilized by autoclave, filtration, or irradiation.

EXAMPLE 21

A 10 mg tablet for oral administration may be prepared from a compound of Formula (I), or a pharmaceutically acceptable salt thereof, e.g. 3,5-dibromo-(3-isopropyl-4-methoxyphenylsulfonyl)phenylacetic acid.

| Ingredients | |
|---|---|
| Compound of Formula (I) | 10 mg |
| Microcrystalline cellulose | 81.9 mg |
| Sodium starch glycolate | 4 mg |
| Lactose | 45 mg |
| Magnesium stearate | 1 mg |
| [Film coat (color & polymers) | 3 mg] |

The active ingredient is milled and mixed with the microcrystalline cellulose, sodium starch glycolate and lactose in a suitable blender. The magnesium stearate is added, the mixture blended to obtain uniformity and the mixture compressed into a tablet. Optionally the tablet is then provided with an aqueous film coating containing color.

EXAMPLE 22

A suppository for rectal administration may be prepared from a compound of Formula (I), or a pharmaceutically acceptable salt thereof, e.g. 3,5-dibromo-4-(4-hydroxy-3-iodophenylsulfonyl)phenylacetic acid, by forming a melt of 100 mg of a compound of Formula (I) and 1900 mg of cocoa butter, pouring the molten mass into suitable molds and allowing to cool.

EXAMPLE 23

Compounds of this invention were screened for their ability to lower cholesterol, according to the assay procedure detailed above, at doses of 10 mg/kg in feed and 50 mg/kg by gavage.

In mice on the normal diet, with test compound in the feed, reductions in serum cholesterol of from 7 to 53% ($P<0.001$) were observed after 7 days of treatment. There were no statistically significant increases in heart weight for most compounds when dosed at 10 mg/kg; however, the compound of Example 14 was associated with a 13% increase ($P<0.001$) in heart weight and the compound of Example 7, a 6% increase ($P<0.05$). These results suggest that it would be preferable to use lower dosing regimens with these compounds.

The compound of Example 3 was found to be effective (14% reduction in 7 days) at doses as low as 0.08 mg/kg when administered in the normal diet feed. Mice on the high fat diet, receiving 10 mg/kg of the compound of Example 3 in feed, showed an 11% reduction ($P<0.01$) in serum cholesterol after 14 days treatment. By gavage, a 37% reduction ($P<0.01$) was observed after 42 days at 1.1 mg/kg.

The following claims particularly point out and distinctly claim that which applicants regard as their invention and are entitled to the full range of legally cognizable equivalents.

What is claimed is:

1. 3,5-dibromo-4-(3-cyclohexyl-4-hydroxyphenylsulfonyl)phenylacetic acid.

2. 3,5-dibromo-4-(3-cyclohexyl-4-methoxyphenylsulfonyl)phenylacetic acid.

* * * * *